United States Patent [19]

Arnould et al.

[11] Patent Number: 4,587,262

[45] Date of Patent: May 6, 1986

[54] HALOGENOPHENYL GLYCERIDE ESTERS FOR USE IN THE PROPHYLAXIS AND/OR THERAPY OF ACNE VULGARIS

[75] Inventors: Jean C. Arnould, Cormonpreuil, France; John R. Evans, Macclesfield, United Kingdom; Geraint Jones, Prestbury, United Kingdom; David S. Thomson, Holmes Chapel, United Kingdom

[73] Assignee: Imperial Chemical Industries PLC, London, England

[21] Appl. No.: 501,758

[22] Filed: Jun. 6, 1983

[30] Foreign Application Priority Data

Jun. 18, 1982 [EP] European Pat. Off. ........ 82401119.1

[51] Int. Cl.$^4$ ..................... A61K 31/235; C07C 69/00
[52] U.S. Cl. ................................ 514/548; 260/410.7; 560/138
[58] Field of Search ........................ 560/138, 146, 194; 424/311, 312, 313; 260/404.8, 408, 410.5, 410.7; 514/548

[56] References Cited

U.S. PATENT DOCUMENTS 3,506,720  4/1970  Model et al. ..................... 260/410.7
3,576,843  4/1971  Model .

FOREIGN PATENT DOCUMENTS 0099177  1/1984  European Pat. Off. ............ 560/138
1038185  8/1966  United Kingdom .

OTHER PUBLICATIONS

E. Franz et al., J. International Medical Research, 1978, vol. 6, pp. 72–77.
Arnould et al., "Chem. Abst.", vol. 101, No. 101: 6818y (1984).
I.C.I. "Chem. Abst.", vol. 101, No. 101: 110556x, Abstract of Japanese Koki 59 51,240.

*Primary Examiner*—Anton H. Sutto
*Attorney, Agent, or Firm*—Cushman, Darby & Cushman

[57] ABSTRACT

The invention concerns novel glyceride esters of antibacterial halogenated phenols having the formula I in which Ra and Rb are independently (3-20C)alkyl or (3-20C)alkenyl; Rc and Rd are independently chloro or bromo; Re is hydrogen, chloro or bromo; and A is (1-6C)alkylene optionally bearing one or two (1-4C)alkyl substituents.

The esters are of use in the prophylaxis and/or therapy of acne vulgaris. Pharmaceutical compositions for topical administration and processes for the manufacture of the esters are also provided.

11 Claims, No Drawings

HALOGENOPHENYL GLYCERIDE ESTERS FOR USE IN THE PROPHYLAXIS AND/OR THERAPY OF ACNE VULGARIS

This invention concerns novel halogenophenyl glyceride esters and, more particularly, novel glyceride esters of anti-bacterial halogenophenols, which esters are useful in the topical therapy and/or prophylaxis of acne vulgaris and related infected skin conditions.

Acne vulgaris is a multi-factorial disease which appears during puberty and affects a high proportion of mankind between the ages of 12 and 25. A major contributory factor is the presence of bacteria within the pilosebaceous follicle coupled with hormone induced hyperactivity of the sebaceous glands. The principal bacterium involved is *Propionibacterium acnes*, which bacterium is to be found towards the base of pilosebaceous follicles and contributes to the inflammatory component of acne, for example by the lipase catalysed production of free fatty acids from sebaceous secretions. It is possible to treat acne vulgaris by systemic administration of potent antibiotics such as tetracycline. However, the use of potent antibiotics for non life-threatening conditions such as acne vulgaris is in general undesirable because of induction of unnecessary bacterial resistance. There is thus a continuing need for a simple alternative form of therapy.

It is known that various halogenophenols are valuable anti-bacterial and disinfectant agents (UK patent specification Ser. No. 1038185). Several of these agents have been used as antibacterials in a variety of skin cleansing and disinfecting preparations. At least one such agent, 2,4,4'-trichloro-2'-hydroxydiphenyl ether (triclosan), has been clinically evaluated in the topical treatment of acne vulgaris (J. Int. Med. Res., 1978, 6, 72–77). However, a major problem in any topical antibacterial treatment of acne is to ensure that the anti-bacterial agent penetrates into, and persists, in the pilosebaceous follicles containing the *P.acnes*. In addition, it is generally desirable to minimise the exposure of other parts of the skin to the anti-bacterial agent. In this way systemic absorption may be reduced. The sebaceous secretion contains various lipid components and improved penetration by an anti-acne agent might be expected to result from an increase in its lipophilicity. Improved persistence might be expected through progressive release of an anti-bacterial agent specifically within the pilosebaceous follicles. We have now discovered various novel, lipophilic glyceride esters of anti-bacterial halogenophenols, which are, unexpectedly, relatively stable towards hydrolysis by esterases, but labile towards hydrolysis by lipases. These esters are expected to be of value in the treatment and/or prophylaxis of acne vulgaris by virtue of progressive, lipase catalysed release of the anti-bacterial halogenophenol within the pilosebaceous follicle in the presence of *P.acnes*.

According to the invention there is provided an ester of the formula I wherein Ra and Rb are independently (3–20C)alkyl or (3–20C)alkenyl; Rc and Rd are independently chloro or bromo; Re is hydrogen, chloro or bromo; and A is (1–6C)alkylene optionally bearing one or two (1–4C)alkyl substituents.

In this specification the terms Ra, Rb, et cetera, are used to depict generic radicals and have no other significance. Formula drawings corresponding to the Roman numerals are attached hereafter.

A particular value for Ra or Rb when it is (3–20C)alkyl is, for example, propyl, butyl, pentyl, hexyl, heptyl, undecyl, pentadecyl or heptadecyl; and when it is (3–20C)alkenyl is, for example 8-heptadecenyl or 8,11-heptadecadienyl.

A particular value for A is, for example, methylene, ethylene, trimethylene or tetramethylene, optionally bearing one or two methyl or ethyl substituents.

A preferred group of esters comprises those compounds of formula I wherein Rc, Rd and Re are all chloro; Ra and Rb are both (3–15C)alkyl; and A has the meanings defined above.

A further preferred group of esters comprises those compounds of formula I wherein Rc, Rd and Re are all chloro, Ra and Rb are both pentadecyl and A is trimethylene optionally bearing 1 or 2 methyl substituents.

Specific esters according to the invention are described in the accompanying Examples. However, of these, the following are of special interest:-2-butyryloxy-1-(butyryloxymethyl)ethyl 5-chloro-2-(2,4-dichlorophenoxy)phenyl glutarate, 5-chloro-2-(2,4-dichlorophenoxy)phenyl 2-octanoyloxy-1(octanoyloxymethyl)ethyl glutarate and 5-chloro-2-(2,4-dichlorophenoxy)phenyl 2-hexadecanoyloxy-1-(hexadecanoyloxymethyl)ethyl glutarate.

The esters of formula I may be obtained by conventional procedure of organic chemistry well known in the art. The invention further provides a process for the manufacture of an ester of formula I by such a conventional procedure, for example as follows, wherein Ra, Rb, Rc, Rd, Re and A have the meanings defined above:-

(a), reacting an acid of the formula II, or a reactive derivative thereof, with a glyceride of the formula III;

(b), reacting an acid of the formula IV or a reactive derivative thereof, with a phenol of the formula V; or (c), reacting an acid of the formula VI, wherein Rf has the same meaning as Ra or Rb, or a reactive derivative therof, with an alcohol of the formula VII, wherein Rg is hydrogen or a group of the formula Ra.CO— or Rb.CO—.

It will be appreciated that procedures (a)–(c) are all general esterification processes well known in the art, which may be performed under generally similar reaction conditions.

Particularly suitable reactive derivatives for acids of formula II or IV are, for example, acid halides (especially acid chlorides or bromides), acid azides, acid anhydrides or mixed anhydrides especially with formic acid or trifluoroacetic acid. Similarly, particularly suitable reactive derivatives for acids of formula VI are, for example, acid halides such as acid chlorides or bromides, and acid anhydrides.

The esterification is generally carried out at a temperature in the range, for example, 0°–100° C.; and conveniently at or near ambient temperature. A suitable solvent or diluent such as chloroform, dichloromethane, 1,2-dimethoxyethane, tetrahydrofuran or diethyl ether is preferably employed.

A suitable base such as pyridine, 2,6-lutidine or triethylamine may also be present and is preferred when an acid halide is used as a reactant. Alternatively, when a reactive derivative of an acid of formula II, IV or VI is employed, the alcoholic or phenolic component of formula III, V or VII may be conveniently used in the form of its salt, such as its sodium, potassium, thallium or lithium salt, which may be preformed in situ by conventional procedures prior to addition of the remaining reagents.

When the free acids of formula II, IV or VI are employed, a condensing agent, for example dicyclohexylcarbodiimide or a mixture of triphenylphosphine and a lower alkyl ester of azodicarboxylic acid, is used in a suitable solvent or diluent.

The starting materials of the formula II may be obtained by acylation of a phenol of formula V with a diacid of the formula: $HO_2C.A.CO_2H$, or an anhydride or acid chloride thereof, using conventional procedures. The glycerides of formula III may be obtained by standard procedures, for example as described by Bentley and McCrae (J. Org. Chem., 1970, 35, 2082). The acids of formula IV may be made by acylation of a glyceride of formula III with a diacid of the formula: $HO_2C.A.CO_2H$, or an anhydride or acid chloride thereof, using conventional procedures. The alcohols of formula VII may be made, for example, using an analogous procedure to (a) above but using a glycerol derivative of the formula VIII in place of the glyceride III and then removing the protecting benzylidene group by a conventional procedure to give the alcohol VII in which Rg is hydrogen. The alcohol VII in which Rg is Ra.CO— or Rb.CO— may then be obtained by careful reaction with one molecular equivalent of the acid VI, or a reactive derivative thereof.

A further convenient procedure (d) for the production of compounds of formula I involves the reaction of a phenol V with a reactive derivative of an acid of the formula: $HO_2C.A.CO_2H$, and a glyceride III. This procedure is a combination of procedures (a) and (b). The reactive derivative is, for example, conveniently the acid chloride or bromide, and the procedure is carried out under generally similar conditions to those for (a) and (b) described above.

It will be appreciated that certain esters of formula I possess one or more asymmetrically substituted carbon atoms, for example when A is (1–6C)alkylene bearing a single (1–4C)alkyl substituent. Such esters may be obtained in racemic and optically active forms. The present invention includes esters of formula I in racemic or optically active form possessing the above mentioned useful properties, which may be demonstrated using the tests described hereinbelow. The preparation of optically active forms may be accomplished by standard means, for example by synthesis from optically active starting materials.

As stated above, the compounds of formula I are unexpectedly more readily hydrolysed by lipases than by esterases. This difference in hydrolytic stability may be demonstrated by a conventional study of the anti-bacterial effects [as measured by minimum inhibitory concentration (M.i.c.)] of the compounds alone and in the presence of added esterase and lipase against the organism Streptococcus faecalis (A02). The results obtained for various representative esters of formula I, exemplified hereinafter, in comparison with the relevant phenol V, in which Rc=Rd=Re=chloro (triclosan), are shown in the Table I below:-

TABLE I

| | M.i.c. (µg/ml) against Streptococcus faecalis (A02) | | | |
|---|---|---|---|---|
| Compound* | Organism only | + 1 mg/ml Esterase A | + 1 mg/ml Esterase B | + 1 mg/ml Lipase C |
| Ester 1 | NA | NA** | NA | 6 |
| Ester 2 | NA | NA | NA | 8 |
| Ester 3 | NA | NA | NA | 10 |
| Ester 4 | NA | NA | NA | 13 |
| Ester 5 | NA | NA | NA | 16 |
| Ester 6 | NA | NA | NA | 10 |
| Ester 7 | NA | NA | NA | 15 |
| Ester 8 | NA | NA | NA | 13 |
| Triclosan | 4 | 8 | 8 | 8 |

*Numbers refer to Examples hereafter.
**Not Active, M.i.c. >256 µg./ml.

Esterase A: ex-porcine liver, pH8 optimum.
Esterase B: ex porcine liver, pH6 optimum.
Lipase C: ex Candida cylindracae.
Enzyme preparations available from Sigma London Chemical Co. Ltd., Poole, UK These results demonstrate the absence of anti-bacterial effects for the esters of formula I except in the presence of added lipase which makes them specially suitable for use in the therapy and/or prophylaxis of acne vulgaris as aforesaid.

The penetration and improved persistence of esters of formula I in pilosebaceous follicles in relation to that of the parent phenol V may be demonstrated under laboratory conditions as follows. The inner surface of rabbit ears is pretreated with coal tar to produce a precomedo type lesion analogous with comedo formation in human acne vulgaris. $^{14}C$-Radio-labelled samples of the test substances are then applied to three areas on the inner surface of the rabbit ear 1,6 and 24 hours prior to killing. In general, samples of esters in a suitable formulation (for example a hydroalcoholic formulation such as a lotion containing 1% w/w ester in a mixture of ethanol, benzyl alcohol and water, 28:30:42 w/w or in a cream formulation such as described in Example 17) are applied to one ear and samples of the parent phenol V in the same vehicle to the contralateral ear. After the animal is killed, each area of application is excised, frozen flat and then biopsied. By gently scraping the surface, residual vehicle and stratum corneum is removed and then digested for estimation of residual radio-activity on the skin surface. Serial frozen sections (20 µm) are then cut from the biopsy, mounted on adhesive tape, freeze dried and autoradiographs produced. From these autoradiographs the relative radioactivity at any depth can be assessed.

As an illustration, using such a procedure, the ester of formula I described in Example 1 hereafter has been found to penetrate to similar depths as its parent phenol (triclosan) but to persist at that depth for longer than the parent phenol. For example, after both 6 and 24 hours the ester described in Example 1 is present deep in the follicles in amounts significantly greater than those of triclosan.

The esters of formula I will be used in the form of various conventional formulations suitable for topical administration. According to a further feature of the invention there is provided a pharmaceutical composition which comprises an ester of formula I as defined hereinbefore together with a pharmaceutically acceptable diluent or carrier in a form suitable for topical administration, for example in the form of an ointment, gel, aqueous or oily solution or suspension, emulsion or aerosol formulation. Normally, compositions which are non-greasy are preferred, and compositions according to this aspect of the invention will generally contain in the range, for example, 0.1–6% w/w and preferably in the range 1–4% w,/w of an ester of formula I.

The pharmaceutical compositions may be made by methods well known in the art for the production of topical formulations, using conventional, pharmaceutically acceptable excipients.

A particular gel formulation may be prepared by adding a gelling agent, for example carboxy-polymethylene, to a solution of an active ingredient as defined above in a suitable organic solvent, for example isopropyl alcohol.

A particular emulsion formulation, for example a cream or a lotion, may be prepared by mixing an active ingredient as defined above with a suitable conventional emulsifying system and water.

The pharmaceutical compositions may also conveniently contain one or more other conventional excipients, for example a solubilising agent such as polyethylene glycol, propylene glycol, diethylene glycol monomethyl or monoethyl ether, or benzyl alcohol, and/or a penetration enhancer such as dimethyl sulphoxide, 1-dodecyl-hexahydro-2H-azepin-2-one, N-methyl-2H-pyrrolidin-2-one or 2H-pyrrolidin-2-one, and/or conventional stabilising agents and antioxidants, in order to produce a stable topical formulation which results in significant absorption of the active ingredient into the pilosebaceous follicles.

The compositions may also contain one or more other active ingredients already known to be of value in the therapy or prophylaxis of acne vulgaris.

When used in the treatment of acne vulgaris it is envisaged that an ester of formula I will be administered so that a daily dose in the range 10–100 $\mu g/cm^2$ is applied to the affected area of the skin, given if necessary in divided doses. However, it will be appreciated that the total daily amount of ester of formula I administered necessarily depends on the extent and severity of the condition under treatment.

The invention will now be illustrated by the following non-limiting Examples each of which constitutes a specific embodiment of the invention and in which, unless otherwise stated:-

(i) petroleum ether (b.p. 60°–80° C.) is referred to as "petrol 60–80";

(ii) evaporations were performed by rotary evaporation in vacuo until all volatile solvents were removed;

(iii) all operations were carried out at ambient temperature, that is in the range 18°–27° C.;

(iv) NMR data relates to protons determined at 60 or 90 MHz and is presented in terms of chemical shift (delta values) relative to an internal standard of tetramethylsilane using conventional abbreviations for description of the absorption signals: s, singlet; d, doublet; t, triplet; m, multiplet; br, broad;

(v) all the esters of formula I had satisfactory elemental microanalyses; and (vi) yields (where given) are for illustration and are not necessarily the maximum attainable:-

EXAMPLE 1

A solution of 2-hydroxy-3-octanoyloxy-propyl octanoate (7.0 g.) and pyridine (1.5 g.) in chloroform (100 ml.) was treated dropwise at 0°–5° C. with a solution of 5-chloro-2-(2,4-dichlorophenoxy)phenyl 4-chloroformylbutyrate (A) (8.4 g.). The reaction mixture was then stirred at ambient temperature for 1 hour and diluted with ether (300 ml.) and water (200 ml). The organic phase was separated, washed successively with 2M hydrochloric acid (50 ml.), saturated sodium bicarbonate solution (3×50 ml.), and then dried ($MgSO_4$) and evaporated. The residual oil was purified by chromatography on silica gel (50 g.) using a mixture of petrol 60–80 and ether (70:30 v/v) as eluant to give 5-chloro-2-(2,4-dichlorophenoxy)phenyl 2-octanoyloxy-1-(octanoyloxymethyl)ethyl glutarate as an oil.(9.1 g.); NMR ($CDCl_3$): 0.9 (6H, t J=4.0 Hz, $CH_3$), 1.1–7 (20H, complex m, $CH_2$), 1.98 (2H,m, $CH_2$), 2.2–2.7 (8H, complex, $CO.CH_2$), 4.0–4.5 (4H,complex, $CH_2O$), 5.25 (1H, br.t J=4.5 Hz, CH), 6.75–7.55 (6H,complex, aromatic H)ppm; mass spectrum (major diagnostic peaks): m/e 585 (16%) [M-0.CO($CH_2$)$_6CH_3$], 441 (21%), 385 (12%), 327 (100%), 288 (10%), 201 (10%), 127 (46%).

The acid chloride (A) was obtained as follows:-

A solution of 5-chloro-2-(2,4-dichlorophenoxy)-phenol (triclosan) (56.8 g.)and glutaric anhydride (90 g.) in tetrahydrofuran (THF) (500 ml.) was heated under reflux for 3 days. The THF was removed by evaporation and the residue mixed with ether (200 ml.). The undissolved solid (unreacted glutaric anhydride) was discarded and the ethereal solution was evaporated. The oil which separated crystallised on trituration with a mixture of ether and petrol 60–80 to give 5-chloro-2-(2,4-dichlorophenoxy)phenyl hydrogen glutarate (39.0 g.), m.p. 84°–85° C. (recrystallised from petrol 60–80/ether).

A mixture of 5-chloro-2-(2,4-dichlorophenoxy)phenyl hydrogen glutarate (16.0 g.) and thionyl chloride (100 ml.) was heated under reflux for 2 hours. The thionyl chloride was then removed by evaporation to give the crude acid chloride(A) as an oil (17.0 g.) (IR 1800 $cm^{-1}$ and 1770 $cm^{-1}$) which was used without purification.

EXAMPLE 2–5

Using a similar procedure to that described in Example 1 but employing the appropriate glyceride of formula III (Ra=Rb) the following esters of the formula IX may be obtained in 40–60% yield:-

EXAMPLE 2

Ra=propyl; oil, NMR ($CDCl_3$): 0.85 (6H, t J=6.6 Hz, $CH_3$), 1.4–2.0 (6H, m, $CH_2$), 2.1–2.6 (8H,m, $COCH_2$), 4.25 (4H,m, $OCH_2$), 5.25 (1H, m, CH), 6.7–7.5 (6H, complex, aromatic H)ppm;

EXAMPLE 3

Ra=undecyl; oil; NMR ($CDCl_3$):0.85 (6H, br.s,$CH_3$), 1.25 (38H, br.s, $CH_2$), 2.0–2.6 (8H,m, $CO.CH_2$), 4.2 (4H,m,$OCH_2$), 6.7–7.5 (6H, complex, aromatic H)ppm:

EXAMPLE 4:

Ra=pentadecyl; oil; NMR ($CDCl_3$): 0.85 (6H, br.s, $CH_3$), 1.25 (54H, br.s, $CH_2$), 2.0–2.7 (8H,m, $CO.CH_2$), 4.25 (4H,m, $OCH_2$), 5.25 (1H,m,CH),6.7–7.5 (6H,complex, aromatic H)ppm; waxy solid, m.p. 36°–38° C. (m.p. 43°–44° C. after recrystallisation from ethanol).

EXAMPLE 5

Ra=8-heptadecenyl; oil; NMR ($CDCl_3$): 0.85 (6H,br.s, $CH_3$); 1.25, 1.8–2.6 (62H,br.s+m, $CH_2+CO.CH_2$), 4.25 (4H,m, $OCH_2$), 5.3 (4H, m, CH=CH), 6.6–7.5 (6H, complex, aromatic H)ppm.

EXAMPLE 6

A solution of 5-chloro-2-(2,4-dichlorophenoxy)-phenol (11.6 g.) and pyridine (3.2 ml.) in chloroform (20 ml.) was added to a solution of succinoyl dichloride (6.2 g.) in chloroform (50 ml.). The mixture was stirred for 10 minutes and then a solution of 3-butyryloxy-2-hydroxypropyl butyrate (9.3 g.) and pyridine (3.2 ml.) in chloroform (20 ml.) was added. The mixture was stirred for 2 hours and then diluted with dichloromethane (50 ml.) and water (100 ml.). The organic phase was washed successively with 2M hydrochloric acid (50 ml.) and saturated sodium bicarbonate solution (2×50 ml.), dried ($MgSO_4$) and evaporated to give an oil (28 g.) which was purified by chromatography on silica gel (500 g.) using a 9:1 v/v mixture of petrol 60–80 and ethyl acetate as eluant. There was thus obtained 2-butyryloxy-1-(butyryloxymethyl)ethyl 5-chloro-2-(2,4-dichlorophenoxy)phenyl succinate as an oil (9.0 g.); NMR ($CDCl_3$): 0.9 (6H, t J=6.6 Hz, $CH_3$), 1.65 (4H, m, $CH_2$), 2.3 (4H, m, $COCH_2$), 2.8 (4H, m, $COCH_2CH_2CO$), 4.25 (4H,m, $OCH_2$), 5.3 (1H, m,CH), 6.7–7.6 (6H, complex, aromatic H)ppm.

EXAMPLE 7

Using a similar procedure to that described in Example 6, but using adipoyl dichloride in place of succinoyl dichloride, there was obtained 2-butyryloxy-1-(butyryloxymethyl)ethyl 5-chloro-2-(2,4-dichlorophenoxy)phenyl adipate as an oil in 35% yield: NMR ($CDCl_3$): 0.95 (6H,t J=6.6 Hz, $CH_3$), 1.7 (8H, m,$CH_2$), 2.3 (8H, m, $COCH_2$), 4.25 (4H,m, $OCH_2$), 5.25 (1H, m, CH), 6.7–7.5 (6H, complex, aromatic H)ppm.

EXAMPLE 8

Using a similar procedure to that described in Example 6, but using 5-chloro-2-(2,4-dichlorophenoxy)-phenol, adipoyl dichloride and 2-hydroxy-3-octanoyloxypropyl octanoate as starting materials, there was obtained 5-chloro-2-(2,4-dichlorophenoxy)-phenyl 2-octanoyloxy-1-(octanoyloxymethyl)ethyl adipate as an oil in 33% yield; NMR ($CDCL_3$): 0.85 (6H, br.s, $CH_3$), 1.25+1.65 (24H, br.s, $CH_2$), 2.3 (8H, m, $COCH_2$), 4.2 (4H, m, $OCH_2$), 5.25 (1H, m, CH), 6.6–7.5 (6H, complex, aromatic H)ppm.

EXAMPLE 9

2-Octanoyloxy-1-(octanoyloxymethyl)ethyl hydrogen glutarate (4.22 g.) was dissolved in dry toluene (40 ml.) and stirred with trifluoroacetic anhydride (5.2 ml.) for 2.5 hours. Triclosan (2.67 g.) was added and the mixture stirred for a further 20 hours. The solution obtained was washed successively with water (2×40 ml.), saturated sodium bicarbonate solution (2×40 ml.) and saturated brine (40 ml.). The organic phase was dried ($MgSO_4$) and evaporated. The oil obtained was chromatographed on silica gel using methylene chloride as eluant to give 5-chloro-2-(2,4-dichlorophenoxy)-phenyl 2-octanoyloxy-1-(octanoyloxymethyl)ethyl glutarate as an oil, having the same NMR and mass spectra as described for the ester in Example 1.

2-Octanoyloxy-1-(octanoyloxymethyl)ethyl hydrogen glutarate was obtained as follows:-

A solution of 2-hydroxy-3-octanoyloxypropyl octanoate (5.0 g.) in ether (30 ml.) was stirred with triethylamine (2.04 ml.) and glutaric anhydride (1.66 g.) for 3.5 hours. Further glutaric anhydride (0.8 g.) was then added together with triethylamine (1.0 ml.). This mixture was heated under reflux until no further starting octanoate could be detected by thin layer chromatography (silica: methylene chloride). The cooled reaction mixture was washed with 1M hydrochloric acid (2×20 ml.), then with water (2×20 ml.), dried ($MgSO_4$) and evaporated to give 2-octanoyloxy-1-(octanoyloxymethyl)ethyl hydrogen glutarate as an oil (6.62 g.); NMR ($CDCl_3$): 0.9 (6H, t, $CH_3$), 1.1–2.1 (22H, m, $CH_2$), 2.4 (8H, m, $CH_2CO$), 4.0–4.4 (4H,m, $CH_2O$), 5.1–5.4 (1H, br.t, CHO), 9.6 (1H, br.s, $CO_2H$)ppm. Mass spectrum (major diagnostic peaks based on M=458, using chemical ionisation techniques): m/e 476 (M+$NH_4$), 360 (M+$NH_4$—$HO_2C.(CH_2)_3.CO_2H$)

EXAMPLE 10

A mixture of cyclohexane (60 ml.), pyridine (1.43 ml.) and 2-hexadecanoyloxy-1-(hexadecanoyloxymethyl)ethyl hydrogen glutarate (B) (11.0 g.) was warmed to 35° C. The solution obtained was added dropwise during 45 minutes to a stirred solution of thionyl chloride (1.23 ml.) in cyclohexane (25 ml.) at 35° C. The mixture was then stirred for a further 1.5 hours at 35° C., cooled to 15° C. and a solution of triclosan (4.68 g.) and pyridine (1.56 ml.) in cyclohexane (20 ml.) added during 15 minutes. The mixture was stirred at ambient temperature for 16 hours, warmed to 35° C. and washed first with 0.5 M hydrochloric acid (100 ml.) and then with water (3×100 ml.), also heated to 35° C. The mixture was then dried ($MgSO_4$) and evaporated to give 5-chloro-2-(2,4-dichlorophenoxy)phenyl 2-hexadecanoyloxy-1-(hexadecanoyloxymethyl)ethyl glutarate as a white solid, m.p. 44°–46° C., identical with the material obtained in Example 4 as judged by its NMR and mass spectral properties.

The hydrogen glutarate (B) was obtained as follows:-

Glutaric anhydride (20.63g.) was added to a solution of 3-hexadecanoyl-2-hydroxypropyl hexadecanoate (1,3-dipalmitin) and triethylamine (25.4 ml.) in cyclohexane (750 ml.) at 40°–45° C. and the mixture was stirred at the same temperature for 16 hours. The hot solution was washed with 0.5M hydrochloric acid (200 ml.) and then with water (3×200 ml.) at 45° C. The cyclohexane layer was separated and, on cooling to about 10° C., deposited 2-hexadecanoyloxy-1-(hexadecanoyloxymethyl)ethyl hydrogen glutarate (B) as a solid (33.2 g., m.p. 59°–59.5° C. after recrystallisation from ethanol).

EXAMPLE 11

Using a similar procedure to that described in Example 1, but starting from 2-hydroxy-3-(hexadecanoyloxy)propyl hexadecanoate (1,3-dipalmitin) and 5-chloro-2-(2,4-dichlorophenoxy)phenyl 4-chloroformyl-2,2-dimethylbutyrate(C), there was obtained 5-chloro-2-(2,4-dichlorophenoxy)phenyl 4-[2-hexadecanoyloxy-1-(hexadecanoyloxymethyl)ethoxycarbonyl]-2,2-dimethylbutyrate (Example 11) as an oil in 33% yield; NMR ($CDCL_3$): 0.6–1.1 (6H, m, $CH_3CH_2$), 1.1–2.1 [60H, m, $\overline{CH_2CH_2}$+$(CH_3)_2C$], 2.2–2.5 $\overline{(6H}$, m, $CH_2CO$), 4.0–4.4 (4$\overline{H}$,m, $CH_2O$), 5.1–5.3 (1H,m, CHO), 6.7–7.5 (6H, m, aromatic H)ppm.

The necessary starting material (C) was obtained by a similar procedure to that described for the acid chloride in Example 1 starting from the appropriate acid (C') which was itself obtained as follows:-

A mixture of triclosan (29.0 g.), triethylamine (15 ml.) and 2,2-dimethylglutaric anhydride (20 g.) was heated at 80° C. for 5 hours. A further quantity (2.0 g.) of anhydride and triethylamine (1 ml.) were added and heating continued for 24 hours. The mixture was cooled to ambient temperature, washed with 2M hydrochloric acid (100 ml.), then with water (3×80 ml.) and dried (MgSO$_4$). The solution obtained was evaporated. The brown residual oil was dissolved in hot cyclohexane. The solution on cooling gave white crystals which were recrystallised from cyclohexane/petrol 60-80 to give 5-chloro-2-(2,4-dichlorophenoxy)phenyl 4-carboxy-2,2-dimethylbutyrate (C') (12.7 g.), m.p. 125°–128° C.

EXAMPLES 12-14

Using a similar procedure to that described in Example 1, the following esters were obtained:-(Example 12): 5-chloro-2-(2,4-dichlorophenoxy)phenyl 4-[2-hexadecanoyloxy-1-(hexadecanoyloxymethyl)ethoxycarbonyl]-3-methylbutyrate as a solid m.p. 28°–29° C.; NMR (CDCl$_3$): 0.7–0.95 (6H,m, CH$_2$CH$_3$), 0.95–1.05 (3H,d, CHCH$_3$), 1.10–1.80 (52H,m,CH$_2$), 2.1–2.4 (8H, m,CH$_2$CO), 2.5 (1H,m, CHCH$_3$), 3.9–4.2 (4H,m, CH$_2$O), 5.1–5.3 (1H,m, CHCO), 6.7–7.45 (6H,m, aromatic H)ppm; in 7% yield starting from 1,3-dipalmitin and 5-chloro-2-(2,4-dichlorophenoxy)phenyl 4-chloroformyl-3-methylbutyrate;

(Examples 13–14): 5-chloro-2-(2,4-dichlorophenoxy)phenyl 4-[2-hexadecanoyloxy-1-(hexadecanoyloxymethyl)ethoxycarbonyl]-2-methylbutyrate (Example 13) and -4-methylbutyrate (Example 14) together as an oil; $^1$H-NMR (CDCl$_3$): 0.75–1.0 (6H,t, CH$_2$CH$_3$), 1.1–2.2 (57H, m, CHCH$_3$+CH$_2$), 2.2–2.9 (7H,m, CH$_2$CO+CHCO), 6.76–7.5 (6H, m, aromatic H)ppm; [Note: $^{13}$C-NMR (CDCl$_3$:22.25 MHz) distinguishes the carbonyl groups of the two isomeric arrangements of the 2-methylglutaric acid moiety and indicates the mixture to contain 72 parts of the 2-methylbutyrate (Ex.13) (phenolic carbonyl 171.52 ppm, glyceride carbonyl 172.76 ppm) and 28 parts of the 4-methylbutyrate (Ex.14) (phenolic carbonyl 169.94 ppm, glyceride carbonyl 174.39 ppm)]; in 83% yield, starting from 1,3-dipalmitin and a mixture of 5-chloro-2-(2,4-dichlorophenoxy)phenyl 4-chloroformyl-2-methylbutyrate and -4-methylbutyrate.

The starting chloroformyl compounds were obtained from the corresponding acids using an analogous procedure to that described for the acid chloride in Example 1. The acids were themselves obtained as follows:-

(a) 5-chloro-2-(2,4-dichlorophenoxy)phenyl 4-carboxy-3-methylbutyrate (D)

A mixture of triclosan (22.3 g.), 3-methylglutaric anhydride (15.0 g.) and triethylamine (15 ml.) in ether (250 ml.) was stirred for 20 hours, and then washed first with 2M hydrochloric acid (50 ml.) and then with water (3×150 ml.). The ether phase was dried (MgSO$_4$) and evaporated. A portion (20 g.) of the residual oil was purified by chromatography on silica gel using methylene chloride as eluant to give (D) as a colourless oil (7.4 g.) ; NMR (CDCl$_3$): 0.8–1.3 (3H,d, CH$_3$), 2.1–2.8 (5H,m,CH$_2$CO+CH$_3$CH), 6.7–7.6 (6H, m, aromatic H), 11.25 (1H,s, CO$_2$H)ppm.

(b) 5-chloro-2-(2,4-dichlorophenoxy)phenyl 4-carboxy-2-methyl-(and-4-methyl)butyrate (E)

Using similar conditions to those described in (a) above, but starting from triclosan (33.9 g.), 2-methylglutaric anhydride (22.6 g.) and triethylamine (30 ml.), the mixture of acids (E) was obtained as an oil (26.7 g.) (after chromatography); NMR (CDCl$_3$): 1.1–1.3 [3H, dd (1.43:1), CH$_3$CH], 1.7–2.2 (2H,m, CHCH$_2$CH$_2$), 2.3–2.9 (3H,m, CHCO+CH$_2$CO), 6.7–7.6 (6H, m, aromatic H), 10.0 (1H,br.s, CO$_2$H)ppm; [Note: the region 2.3–2.9 contains 2 overlapping multiplets ca 2.3–2.6 ppm and ca 2.5–2.9 ppm assigned to the 2-methyl-and 4-methylbutyrates, respectively].

EXAMPLE 15

A mixture of 2-hexadecanoyloxy-1-(hexadecanoyloxymethyl)ethyl 4-chloroformyl-3,3-dimethylbutyrate (F) (1.5 g.), triclosan (0.4 g.) and pyridine (0.17 ml.) in methylene chloride (35 ml.) was stirred at 0°–5° C. for 3 hours and then allowed to attain ambient temperature during 45 hours. The methylene chloride was evaporated and replaced by ether (50 ml.). The mixture obtained was washed successively with water (3×20 ml.), 2M hydrochloric acid (25 ml.), saturated sodium hydrogen carbonate solution (2×20 ml.) and water (2×20 ml.), and then dried (MgSO$_4$) and evaporated. The oil obtained crystallised on treatment with ethanol to give 5-chloro-2-(2,4-dichlorophenoxy)phenyl 4-[2-hexadecanoyloxy-1-(hexadecanoyloxymethyl)ethoxycarbonyl]-3,3-dimethylbutyrate as white crystals (0.3 g.), (m.p. just below 20° C.); NMR (CDCl$_3$): 0.7–1.0 (6H, m, CH$_3$CH$_2$), 1.12 (6H, s, CCH$_3$), 1.15–1.7 (52H,m, CH$_2$), 2.17 (4H, m, CH$_2$CH$_2$CO), 2.44 (2H,s, CH$_2$CO$_2$CH), 2.60 (2H, s, aromatic O.CO CH$_2$), 3.9–4.4 (4H, m, CH$_2$O), 5.1–5.4 (1H, m, CH$_2$CO$_2$CH), 6.9–7.5 (6H, m, aromatic H)ppm.

The starting acid chloride (F) was obtained as follows:-

3,3-Dimethylglutaric anhydride (5.0 g.) and benzyl alcohol (11 ml.) were heated together at 150° C. for 16 hours. The cooled reaction mixture was partitioned between saturated sodium carbonate solution (50 ml.) and ether (50 ml.). The aqueous layer was separated, acidified with 2M hydrochloric acid and extracted with ether. The extracts were evaporated. The residual yellow oil (4.6 g.) was purified by chromatography on silica gel with methylene chloride as eluant to give benzyl hydrogen 3,3-dimethylglutarate as an oil (1.5 g.); NMR (CDCl$_3$): 1.1 (6H,s, CH$_3$), 2.45+2.47 (4H, 2s, COCH$_2$), 5.12 (2H,s, OCH$_2$), 7.37 (5H, s, aromatic H), 8.45 (1H, br.s, CO$_2$H)ppm. This benzyl ester (1.5 g.) was dissolved in methylene chloride (15 ml.) and stirred with thionyl chloride (2.2 ml.) and N,N-dimethylformamide (DMF) (0.3 ml.) for 3 hours. The solvent was evaporated and the residue was dissolved in dry toluene (15 ml.) and the solution re-evaporated. This was repeated twice to remove excess thionyl chloride. The residual oil (1.5 g.) containing crude benzyl 4-chloroformyl-3,3-dimethylbutyrate was dissolved in methylene chloride (25 ml.). The solution was added to a cooled solution of 1,3-dipalmitin (1.4 g.) in methylene chloride (25 ml.) containing pyridine (0.32 ml.). The mixture was stirred for 2 hours at 0°–5° C. and then for 46 hours at ambient temperature. The solvent was evaporated and the residue was partitioned between ether (70 ml.) and water (3×25 ml.). The organic phase was washed with 2M hydrochloric acid, saturated sodium hydrogen carbonate solution (2×25 ml.) and finally with water (2×25 ml.), and then dried (MgSO$_4$) and evaporated. The residual oil crystallised on treatment with ethanol to give 2-hexadecanoyloxy-1-(hexadecanoyloxymethyl)ethyl 4-benzyloxycarbonyl-3,3-dimethylbutyrate as a white solid (2.5 g.).

This material was dissolved in warm ethanol (50 ml.), mixed with 10% w/w palladium-on-charcoal catalyst (0.5 g.) and hydrogenated at atmospheric pressure. The catalyst was removed by filtration of the heated mixture. The filtrate was evaporated to give 2-hexadecanoyloxy-1-(hexadecanoyloxymethyl)ethyl hydrogen 3,3-dimethylglutarate as an oil (1.5 g.) which was converted to its acid chloride (F) with thionyl chloride and DMF as described above for benzyl 4-chloroformyl-3,3-dimethylbutyrate. The acid chloride (F) was obtained as an oil which was used immediately in the above reaction with triclosan.

EXAMPLE 16

Using a similar procedure to that described in Example 10, but replacing triclosan by 2-(2,4-dibromophenoxy)-5-chlorophenol, there was obtained 2-(2,4-dibromophenoxy)-5-chlorophenyl 2-hexadecanoyloxy-1-(hexadecanoyloxymethyl)ethyl glutarate as an oil in 16% yield; NMR (CDCl$_3$): 0.7–1.05 (6H, t, CH$_3$), 1.05–1.86 (52H, m, CH$_2$), 1.86–2.2 (2H,m, COCH$_2$CH$_2$CH$_2$CO), 2.2–2.7 (8H,m, CH$_2$CO), 3.94–4.42 (4H,m, CH$_2$O), 5.1–5.4 (1H,m, CHO), 6.7–7.8 (6H,m, aromatic H)ppm.

EXAMPLES 17–21 (Components given in % w/w)

Typical pharmaceutical compositions containing as active ingredient an ester of formula I may be prepared by conventional procedures and with the following constitutions:-

(EXAMPLE 17)

Cream:
 active ingredient 1
 isopropyl myristate 10
 cetostearyl alcohol 5
 'Arlacel' 165 2
 propylene glycol 5
 ethanol (95%) 5
 purified water to 100

['Arlacel' 165 is a trade-mark for a glyceryl monostearate/polyethylene glycol 100 stearate blend, available from ICI Americas Inc. Wilmington, Delaware, USA].

(EXAMPLE 18)

Lotion 1:
 active ingredient 1
 cetostearyl alcohol 5
 'Brij' 52 5
 isopropyl alcohol 5
 purified water to 100

['Brij' 52 is a trade-mark for polyoxyethylene cetyl ether available from ICI Americas Inc.]

(EXAMPLE 19)

Lotion 2 liquid cream):
 active ingredient 3
 cetostearyl alcohol 2.5
 isopropyl myristate 6
 sorbitan monostearate 1.5
 polysorbate 60 1.5
 ethanol (95%) 6.5
 purified water to 100

(EXAMPLE 20)

Lotion 3:
 active ingredient 0.5
 propylene glycol 20
 ethanol (95%) 40
 purified water to 100

(EXAMPLE 21)

Gel:
 active ingredient 0.5
 propylene glycol 20
 ethanol (95%) 40
 'Carbopol' 934 1
 [sodium hydroxide (10% w/v) to adjust to pH 5.5]
 purified water to 100

['Carbopol' 934 is a trade-mark for a gelling agent available from Goodrich-Wright Inc., Dallas, Texas, USA].

A conventional preservative such as methyl and/or propyl paraben or other excipient may be incorporated in the above compositions if desired.

In general the compositions described in Examples 17 and 19 are suitable for use with any of the esters of formula I described hereinbefore. However, the hydroalcoholic compositions described in Examples 18, 20 and 21 are normally preferred for use with those esters of formula I wherein Ra and Rb are (3–10C)alkyl because of the decreasing alcoholic solubility of the other esters as the size of the alkyl groups Ra and Rb is increased.

The esters of formula I described in the above Examples may be summarised as follows:-

| Example No. | Ra.CO (=Rb.CO) | Rd (=Re) | A |
|---|---|---|---|
| 1 | octanoyl | chloro | —CH$_2$CH$_2$CH$_2$— |
| 2 | butyryl | chloro | —CH$_2$CH$_2$CH$_2$— |
| 3 | dodecanoyl | chloro | —CH$_2$CH$_2$CH$_2$— |
| 4 | hexadecanoyl (palmitoyl) | chloro | —CH$_2$CH$_2$CH$_2$— |
| 5 | 9-octadecenoyl (oleoyl) | chloro | —CH$_2$CH$_2$CH$_2$— |
| 6 | butyryl | chloro | —CH$_2$CH$_2$— |
| 7 | butyryl | chloro | —CH$_2$CH$_2$CH$_2$CH$_2$— |
| 8 | octanoyl | chloro | —CH$_2$CH$_2$CH$_2$CH$_2$— |
| 9 | octanoyl | chloro | —CH$_2$CH$_2$CH$_2$— |
| 10 | hexadecanoyl | chloro | —CH$_2$CH$_2$CH$_2$— |
| 11 | hexadecanoyl | chloro | —C(CH$_3$)$_2$CH$_2$CH$_2$— |
| 12 | hexadecanoyl | chloro | —CH$_2$CH(CH$_3$)CH$_2$— |
| 13 | hexadecanoyl | chloro | —CH(CH$_3$)CH$_2$CH$_2$— |
| 14 | hexadecanoyl | chloro | —CH$_2$CH$_2$CH(CH$_3$)— |
| 15 | hexadecanoyl | chloro | —CH$_2$C(CH$_3$)$_2$CH$_2$— |
| 16 | hexadecanoyl | bromo | —CH$_2$CH$_2$CH$_2$— |

In all the above esters Rc=chloro and, when A is asymmetrically substituted, the left-hand carbon atom is attached to the aromatic ester group.

Formulae

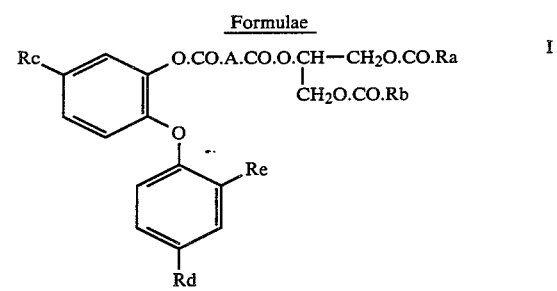

I

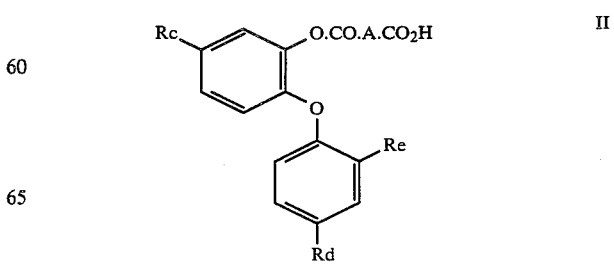

II

-continued
Formulae

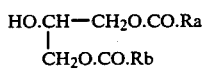

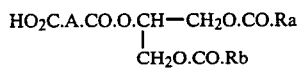

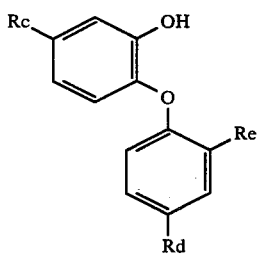

Rf.CO₂H

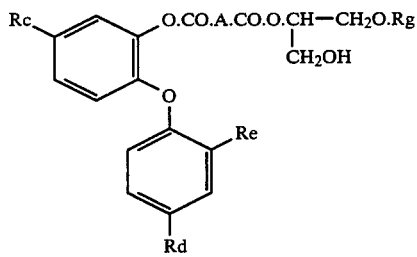

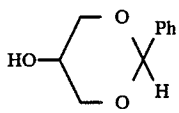

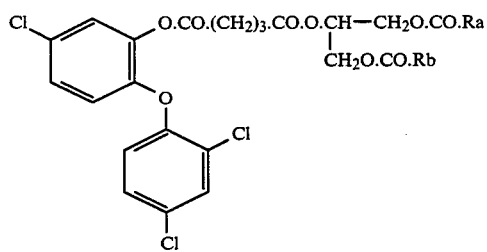

What is claimed is:

1. An ester of the formula I

wherein Ra and Rb are independently selected from (3–20C)alkyl and (3–20C)alkenyl; Rc and Rd are independently selected from chloro or bromo; Re is hydrogen, chloro or bromo; and A is (1–6C)alkylene optionally bearing one or two (1–4C)alkyl substituents.

2. A method for the prophylaxis or therapy of acne vulgaris affecting a warm-blooded animal which comprises administering to the skin of said animal a prophylactically or therapeutically effective amount of an ester of the formula I as claimed in claim 1.

3. An ester according to claim 1, wherein Ra and Rb are independently selected from propyl, butyl, pentyl, hexyl, heptyl, undecyl, pentadecyl, heptadecyl, 8-heptadecenyl and 8,11-heptadecadienyl; Rc, Rd and Re have the meanings defined in claim 1; and A is methylene, ethylene, trimethylene or tetramethylene optionally bearing one or two methyl or ethyl substituents.

4. An ester of the formula I wherein Ra and Rb are both (3–15C)alkyl; Rc, Rd and Re are all chloro; and A is methylene, ethylene, trimethylene or tetramethylene optionally bearing one or two methyl or ethyl substituents.

5. An ester of the formula I wherein Ra and Rb are both pentadecyl; Rc, Rd and Re are all chloro; and A is trimethylene optionally bearing 1 or 2 methyl substituents.

6. 2-Butyryloxy-1-(butyryloxymethyl)ethyl-5-chloro-2-(2,4-dichlorophenoxy)phenyl glutarate or 5-chloro-2-(2,4-dichlorophenoxy)phenyl 2-octanoyloxy-1-(octanoyloxymethyl)ethyl glutarate.

7. 5-Chloro-2-(2,4-dichlorophenoxy)phenyl 2-hexadecanoyloxy-1-(hexadecanoyloxymethyl)ethyl glutarate.

8. A pharmaceutical composition which comprises an ester of formula I, as claimed in claim 1, together with a pharmaceutically acceptable diluent or carrier and in a form suitable for topical administration.

9. A composition as claimed in claim 8 which is an ointment, gel, aqueous or oily solution or suspension, emulsion or aerosol formulation.

10. A composition as claimed in claim 8 wherein the active ingredient is present at a concentration of 0.1 to 6% w/w.

11. A composition as claimed in claim 8 wherein the active ingredient is 5-chloro-2-(2,4-dichlorophenoxy)-phenyl 2-hexadecanoyloxy-1-(hexadecanoyloxymethyl)ethyl glutarate.

* * * * *